(12) United States Patent
Krishna et al.

(10) Patent No.: US 9,102,589 B2
(45) Date of Patent: Aug. 11, 2015

(54) REACTIVE DISTILLATION PROCESS FOR PREPARATION OF ACETAMINOPHEN

(75) Inventors: Arumugam Bhaskar Krishna, Hyderabad (IN); Abul Hasnat, Hyderabad (IN); Sirisha Pamidipati, Hyderabad (IN)

(73) Assignee: GRANULES INDIA LIMITED, Hyderabad (IN)

( * ) Notice: Subject to any disclaimer, the term of this patent is extended or adjusted under 35 U.S.C. 154(b) by 928 days.

(21) Appl. No.: 13/194,873

(22) Filed: Jul. 29, 2011

(65) Prior Publication Data

US 2012/0065423 A1    Mar. 15, 2012

Related U.S. Application Data

(60) Provisional application No. 61/369,417, filed on Jul. 30, 2010.

(51) Int. Cl.
| | | |
|---|---|---|
| *C07C 231/02* | (2006.01) | |
| *B01D 1/22* | (2006.01) | |
| *B01D 3/00* | (2006.01) | |
| *C07C 67/08* | (2006.01) | |
| *C07C 67/54* | (2006.01) | |

(52) U.S. Cl.
CPC .............. *C07C 231/02* (2013.01); *B01D 1/22* (2013.01); *B01D 1/225* (2013.01); *B01D 3/009* (2013.01); *C07C 67/08* (2013.01); *C07C 67/54* (2013.01)

(58) Field of Classification Search
None
See application file for complete search history.

(56) References Cited

U.S. PATENT DOCUMENTS

| | | |
|---|---|---|
| 3,042,719 A | 7/1962 | Hahn et al. |
| 3,076,030 A | 1/1963 | Freifelder |
| 3,113,150 A | 12/1963 | Young |
| 3,341,587 A | 9/1967 | Duesel et al. |
| 3,748,358 A | 7/1973 | Baron |
| 3,781,354 A | 12/1973 | Kosak |
| 4,264,525 A | 4/1981 | Huber, Jr. |
| 4,264,526 A | 4/1981 | Ruopp et al. |
| 4,435,595 A | 3/1984 | Agreda et al. |
| 4,474,985 A | 10/1984 | Keel et al. |
| 4,524,217 A | 6/1985 | Davenport et al. |
| 4,565,890 A | 1/1986 | Sathe |
| 4,670,589 A | 6/1987 | Van Ness et al. |
| 5,155,269 A | 10/1992 | Dunn et al. |
| 5,344,979 A | 9/1994 | Zey et al. |
| 5,648,535 A | 7/1997 | Foster et al. |
| 5,856,575 A | 1/1999 | Gopinathan et al. |
| 5,981,799 A | 11/1999 | Fruchey et al. |
| 6,215,024 B1 | 4/2001 | Choudary et al. |
| 6,277,783 B1 | 8/2001 | Fruchey et al. |
| 6,586,609 B2 | 7/2003 | Ruggieri et al. |

FOREIGN PATENT DOCUMENTS

| | | |
|---|---|---|
| CS | 223945 | 11/1983 |
| EP | 1627041 B1 | 11/2009 |
| IN | 580/MUM/2000 | 7/2005 |

*Primary Examiner* — Yevegeny Valenrod
(74) *Attorney, Agent, or Firm* — Birch, Stewart, Kolasch & Birch, LLP

(57) ABSTRACT

The present invention relates to continuous processes for the preparation of primary and secondary N-acetylated aromatic amines of formula I or O-acetylated product of o-hydroxy benzoic acid of Formula II using acetic acid as an acetylating agent.

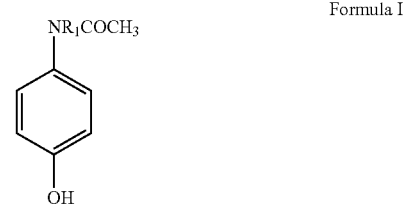

Formula I wherein $R_1$ has a definition of hydrogen atom, $C_1$-$C_4$ alkyl group or $C_1$-$C_4$ alkoxy group.

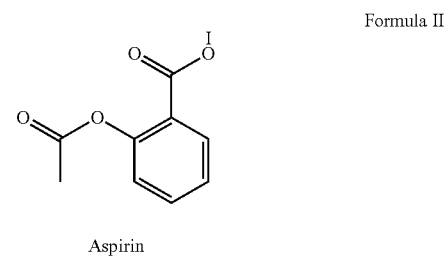

Formula II

Aspirin

21 Claims, 2 Drawing Sheets

REACTIVE DISTILLATION PROCESS FOR PREPARATION OF ACETAMINOPHEN

This Nonprovisional application claims priority benefit under 35 U.S.C. §119(e) of Provisional Patent Application No. 61/369,417 filed on Jul. 30, 2010.

FIELD OF INVENTION

The present invention relates to continuous processes for the preparation of primary and secondary N-acetylated aromatic amines of formula I or O-acetylated product of hydroxy benzoic acid of Formula II using acetic acid as an acetylating agent.

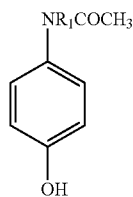

Formula I wherein $R_1$ has a definition of hydrogen atom, $C_1$ to $C_4$ alkyl group or $C_1$ to $C_4$ alkoxy group.

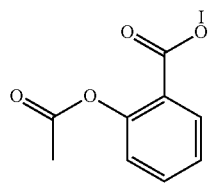

Formula II

Aspirin

BACKGROUND & PRIOR ART OF THE INVENTION

Continuous Reactors
CSTR:

The continuous stirred-tank reactor (CSTR), also known as vat- or backmix reactor, is a common ideal reactor type in chemical engineering. A CSTR often refers to a model used to estimate the key unit operation variables when using a continuous agitated-tank reactor to reach a specified output. CSTR is extensively used in chemical industry.
PFR:

Plug flow reactors are tubular reactors or sometimes called as piston flow reactors. The key assumption is that as a plug flows through a PFR, the fluid is perfectly mixed in the radial direction but not in the axial direction (forwards or backwards). Each plug of differential volume is considered as a separate entity, effectively an infinitesimally small batch reactor, limiting to zero volume. As it flows down the tubular PFR, the residence time (t) of the plug is a function of its position in the reactor. Plug flow reactors have a high volumetric unit conversion, run for long periods of time without maintenance, and the heat transfer rate can be optimized by using more, thinner tubes or fewer, thicker tubes in parallel. Disadvantages of plug flow reactors are that temperatures are hard to control and can result in undesirable temperature gradients. PFR maintenance is also more expensive than CSTR maintenance. There are couple of examples where PFR has been extensively used: for fast and high temperature reactions like low density polyethylene reaction in large scale.

Reactive Separation:
Reactive Distillation:

Reactive Distillation (RD) is a combination of reaction and distillation in one unit operation owing to which it enjoys a number of specific advantages over conventional sequential approach of reaction followed by distillation or other separation techniques. Reactive distillation has been widely used for esterification reactions. This technique may be effectively used to improve the conversion of a reversible reaction by continuously removing one or more of the products.

Reactive distillation is a process where both the chemical reactions and the removal of the products happen simultaneously thus favoring the equilibrium limited reactions to a great extent. The reaction and the separation are normally carried out in a distillation column where three distinct zones exist viz. middle reaction zone, rectification zone at the top and stripping zone at the bottom of the column. The reaction can be accelerated using either homogeneous or heterogeneous catalysts in the reaction. A suitably designed reactive distillation column provides 100% conversion of reactant. The following advantages are obtained if the reaction is carried out in reactive distillation mode.

Improved efficiency due to better component separation
Lower costs—reduced equipment use, energy use and handling
Less waste and fewer byproducts
Improved product quality—reducing opportunity for degradation because of less heat The most spectacular benefits of RD are in the production of methyl acetate (U.S. Pat. No. 4,435,595, April 1982). The acid catalyzed reaction MeOH+AcOH$\rightleftharpoons$MeOAc+$H_2$O which was traditionally carried out in one batch reactor and a train of nine distillation columns In RD implementation only one column is required and nearly 100% conversion of reactant is achieved.

However, the prior art does not report reactive distillation process to carry out the p-aminophenol and acetic acid reaction for the preparation of Paracetamol.
Membrane Reactor:

When a chemical reactor uses a membrane to aid or enhance the reactions by selectively separating products from the reaction mixtures or distributes products in different zones is called a membrane reactor. The main requirement of a membrane reactor is to have a semipermeable medium which selectively permits one of the products to pass through while retaining others. In particular, membrane bioreactors are applied extensively for the manufacture of biological products using enzyme reactions, and are common in the pharmaceutical/biomedical industry. They enhance the sustainability of a process by replacing more energy-intensive techniques such as distillation and evaporation. They are also operationally much simpler, and can be made to be highly selective to the specific desired process (EP 1 627 041 B1).
Pervaporation Unit:

Pervaporation: is a process in which a liquid stream containing two or more components is placed in contact with one side of a non-porous polymeric membrane while a vacuum or gas purge is applied to the other side. The components in the liquid stream sorb into the membrane, permeate through the membrane, and evaporate into the vapor phase. The vapor, referred to as "the permeate", is then condensed. Due to different species in the feed mixture having different affinities for the membrane and different diffusion rates through the membrane, a component at low concentration in the feed can be highly enriched in the permeate. Further, the permeate composition may widely differ from that of the vapor evolved after a free vapor-liquid equilibrium process. Concentration factors range from the single digits to over 1,000, depending on the compounds, the membrane, and process conditions. In comparison with distillation, pervaporation is usually a more energy-saving process because the selectivity is largely improved because of the permselectivity of the membrane.

The applications of pervaporation processes for dehydration from alcoholic solutions and removal of organics from aqueous solutions have been carried out commercially for several years.

Chromatographic Reactor:

Chromatographic reactors integrate chemical reaction and chromatographic separation in one apparatus. This offers potential for process intensification, especially in the case of equilibrium reactions. Different types of discontinuous and continuous processes as well as modeling of chromatographic reactors are available. Synthesis and design of this processes is very much influenced and often restricted by the type of reaction and the operating window which is set by the individual operating conditions for chemical reaction, mass separation, and equipment design. Integrated chromatographic reactors should be considered if chromatography is the favored separation process for a conventional sequential process design. Synthesis of MTBE directly from methanol and tert-butyl alcohol is efficiently carried out in this type of reactor (Process for esterification in a chromatographic reactor, U.S. Pat. No. 6,586,609 July 2003).

U.S. Pat. No. 3,042,719, Jul. 3, 1962, discloses the purification of crude discolored N-acetyl-para-aminophenol (APAP) by acidifying an aqueous solution of the APAP with a mineral acid filtering the solution while hot. Filtrate cooled while adding an alkaline reducing sulfite e.g., sodium hydro sulfite U.S. Pat. No. 3,113,150, Dec. 3, 1963, describes the preparation of pure APAP by neutralizing the wet APAP with ammonium hydroxide to remove excess acetic acid.

U.S. Pat. No. 3,748,358, Jul. 24, 1973, reveals the purification process of APAP by treating it with an acidic solution and then treating it in aqueous solution with carbon.

U.S. Pat. No. 3,781,354, Dec. 25, 1973, describes APAP purification by treating it in hot aqueous solution with ferric chloride and removing color by activated carbon.

U.S. Pat. No. 4,524,217, Jun. 18, 1985, describes a novel process for the preparation of APAP involving two steps. First step involves reacting 4-Hydroxyacetophenone with hydroxylamine salt and a base to obtain the ketoxime and subsequently Beckmann rearrangement of Ketoxime in the presence of catalyst to form APAP.

U.S. Pat. No. 4,264,526, Apr. 28, 1981, describes a process for the production of aminophenols and N-acetyl-p-aminophenol (APAP) comprising alkaline hydrolysis of halonitrobenzene to nitrophenol and from nitrophenols to aminophenols using a borate ion additive during hydrogenation to eliminate undesirable by-products and color formation.

U.S. Pat. Nos. 4,264,525, 4,565,890, 3,076,030, 3,341,587 and 5,155,269, describes acetylation of p-amino phenol was performed in the presence of acetic anhydride in aqueous solvent system. In U.S. Pat. No. 4,264,525 where batch process of acetylation is described. Quality of the APAP was good, giving only a slight pink caustic test and the product yield was 81.2%

CS Patent 223,945 (Cl. C07C 91/44) Nov. 15, 1985 discloses a process wherein the acetylation of aminophenols with acetic anhydride in ethyl acetate or AcOH resulting in moderate yields of acetaminophen.

However, the drawback in most of the above mentioned process is the use of acetic anhydride as acetylating agent.

U.S. Pat. No. 4,565,890, January 21, describes a process wherein N-acetyl-p-aminophenol is prepared wherein p-aminophenol is acetylated in aqueous medium to produce a crude aqueous reaction mixture.

U.S. Pat. No. 4,670,589, Jun. 2, 1987 describes a process for the production of APAP by hydrogenation of p-nitrophenol to p-amino phenol (PAP), and concurrently acetylating the PAP with acetic anhydride.

U.S. Pat. No. 5,648,535, Jul. 15, 1997, describes a process for the production of N-acylaminophenols by the concurrent hydrogenation of a nitrophenol to an aminophenol and the acylation of the aminophenol with acyl anhydride on a continuous basis in a stirred tank reactor. The drawbacks in the above processes are the use of excess acetic anhydride as acetylating agent, difficulty in restricting to mono-acetylation of the amino group, longer reaction times, oligomerization of the hydroxyl aromatic amine, and color body formation.

U.S. Pat. No. 5,856,575, Jan. 5, 1989, describes a process for the manufacture of APAP which process comprises reacting an appropriate phenol and an amide in the presence of a heteropoly acid or its alkali metal salt catalyst.

U.S. Pat. No. 6,215,024, April 10, describes a novel step process for the production of amides from amines comprising reaction of amines with an acylating agent comprising of a carboxylic acid in a molar ratio of 1:3 to 1:10.

Indian patent Nos. IN2000MU00580, Jun. 22, 2000 describes a batch process for preparation of N-acetylated product of primary and secondary aromatic amines produced by N-acetylation of amines by heating with acetic acid, precipitating the product formed by adding water in conventional way, and recrystalising the N-acetylated product.

The aforementioned prior art processes have several limitations associated which is enumerated as follows:

Use of narcotic reagent acetic anhydride for acylation.

Batch process using acetic acid as acylating reagent leading to prolonged reaction time and lack of total completion of the reaction.

Prolonged reaction time for acetylation leading to colored product and formation of undesirable products as impurities.

Low yield <82% of the final product.

Cost ineffective processes.

Non ecofriendly processes.

Hence, there was a long awaited need to develop a process obviating the above limitations. Applicant has now developed a continuous process for the preparation of N-acylated products of primary and secondary aromatic amines and O-acetylated product of hydroxy benzoic acid using acetic acid as an acetylating agent in improved yield and cost effective.

OBJECT OF THE INVENTION

The objective of the present work is to adapt the continuous reaction and the downstream product separation processes instead of conventional batch process using acetic acid as the acetylating agent. The continuous reaction can be carried out in continuous reactors such as a series of steady state continuous stirred tank reactor or in plug flow reactors or in combination of the above. Further improvement in continuous reaction is achieved by carrying out the acetylation in reactive distillation processes wherein simultaneous reaction and separation of the products are efficiently accomplished. Reactive separation techniques employed in the present invention could be any one of the techniques namely reactive distillation, membrane reactor, pervaporation unit and chromatographic reactors. A combination of CSTR or PFR to perform the reaction partially or completely followed by reactive distillation process can also be used to achieve the desirable product in enhanced yield and required purity. The continuous process offers better yield, color, increased throughput, reduces cost of production and less ecological loads. The reaction schemes in this invention are as follows:

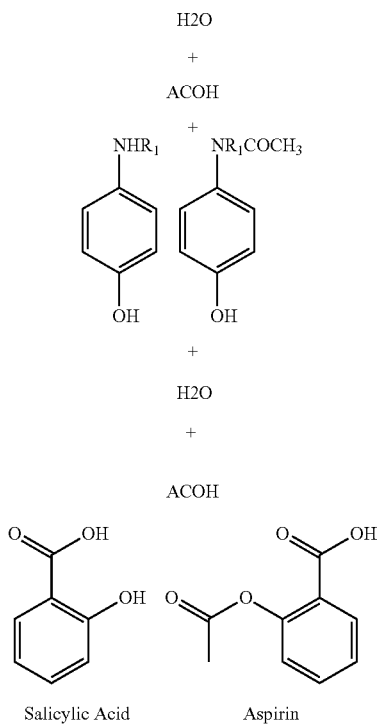

The definition of R1 is as defined above.

Since the above reactions are equilibrium limited, removal of water by some means while reaction is proceeding will shift the equilibrium towards the right thereby increasing the reaction rate significantly. This reduces the reaction time by more than half. Hence shorter exposure of reactants to temperature reduces the formation of impurities, improves the color of product enabling use of less quantity of water and carbon for charcoalization in the work up of reaction mixture thereby increasing the overall yield.

SUMMARY OF THE INVENTION

Figure 1:
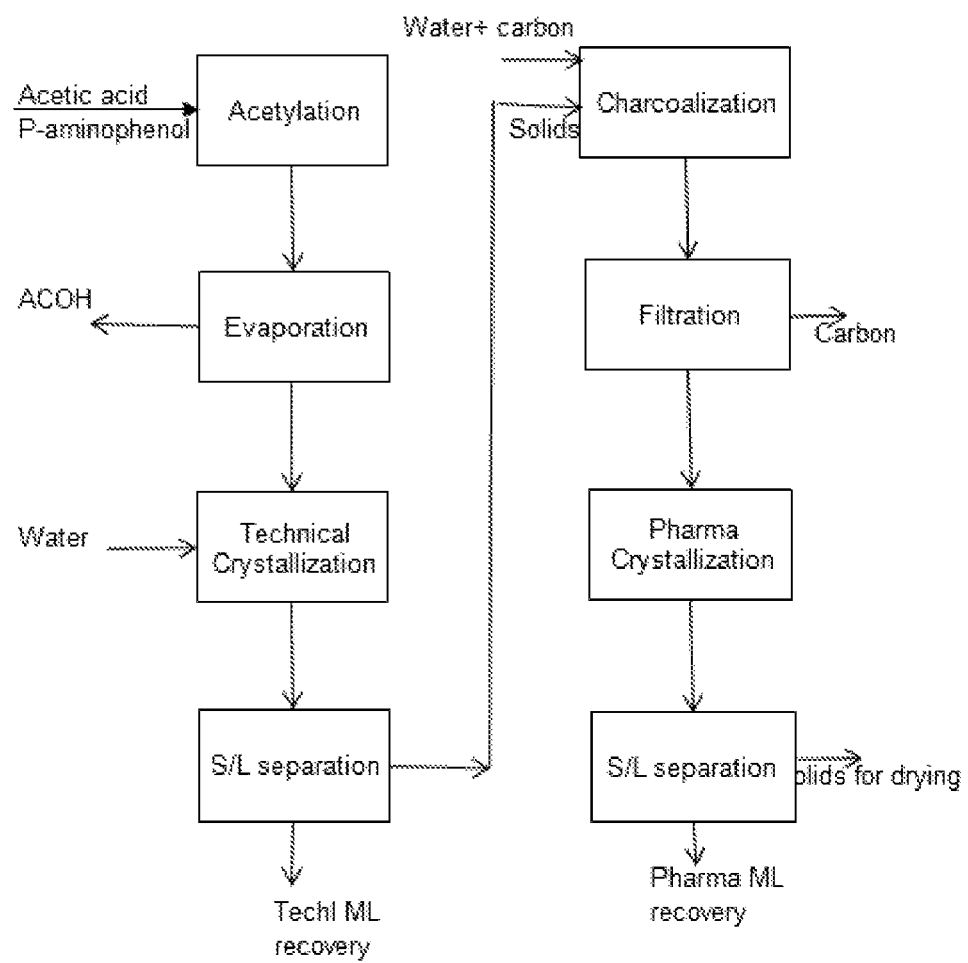
FIG. 1 refers to the flow diagram of the process
FIG. 2 refers to the Reactive distillation unit

The present invention relates to continuous processes for the preparation of primary and secondary N-acetylated aromatic amines or O-acetylated product of hydroxy benzoic acid using acetic acid as an acetylating agent. More particularly, the invention relates to the acylation of paraminophenol or N-ethylparaminophenol or salicylic acid using acetic acid as acetylating agent.

DETAILED DESCRIPTION OF PRESENT INVENTION

In accordance with the present invention, provides continuous process for the acetylation of primary or secondary aromatic amines to manufacture primary or secondary N-acetylated aromatic amines or acylation of hydroxy benzoic acid to manufacture its O-acetylated product comprising the steps of a continuous process comprising the steps of:
  (a) reacting primary or secondary aromatic amines or hydroxy benzoic acid with acetic acid using a unit operation selected from Continuous Stirred Tank Reactors (CSTRs) or a Plug Flow Reactor (PFR) to obtain partially converted product stream;
  (b) subjecting the partially converted product stream obtained in step (a) to a separation process to obtain an enriched product stream;
  (c) optionally adding very low amount of acetic anhydride to the enriched product stream of step (b).

In an embodiment of the invention, the unit operation such as series of Continuous Stirred Tank Reactors (CSTRs) or a Plug Flow Reactor (PFR) process is used in combination with separation process for the acetylation of primary and secondary N-aromatic amines to manufacture primary and secondary N-acetylated aromatic amines or the acetylation of hydroxy benzoic acid—to manufacture its O-acetylated product.

In another embodiment of the invention the separation process is selected from a reactive distillation process, or a membrane separation process, or a pervaporation process, or a chromatographic process.

In yet another embodiment of the invention the primary aromatic amine or secondary aromatic amine or hydroxybenzoic acid is selected from the group consisting of para amino phenol (PAP), n-ethyl p-aminophenol or o-hydroxy benzoic acid, m-hydroxy benzoic acid and p-hydroxy benzoic acid.

In further embodiment of the invention the primary aromatic amine is para amino phenol (PAP) and secondary aromatic amine is N-ethylparaminophenol.

In further embodiment, the hydroxy benzoic acid is salicylic acid.

In yet another embodiment of the invention provides
  the concentration of primary or secondary aromatic amines or hydroxy benzoic acid is less than 50% by weight, preferably 10 to 40% by weight.
  the concentration of acetic acid in primary or secondary aromatic amines or hydroxy benzoic acid is greater than 50% by weight, preferably 60 to 90% by weight.
  the separation process is carried out in temperature range from 60 to 140° C., preferably from 85 to 125° C. and at about atmospheric pressure.

In still another embodiment of the invention provides a process, wherein the enriched reaction mixture obtained is greater than 60%, preferably >90%, most preferably >98% of product.

In still yet another embodiment of the invention provides a process, wherein the enriched product stream is processed comprising the steps of:
  crystallizing by batch or continuous crystallizer;
  separating the crystallized solids and technical mother liquor (technical) by a conventional method;
  re-dissolving the crystallized solids thus obtained in water;
  treating the solution of step (c) with activated carbon or a solid adsorbent such as Dowex L285 and filtering to get a clear solution;

recrystallizing the solution of step (d) in batch or continuous crystallizer;
separating the crystallized solids from mother liquor (pharma) by conventional method;
drying the crystallized solids using a batch dryer such as a fluid bed dryer or a continuous dryer such as Spin Flash dryer;
milling and blending the dried solid.

In further embodiment of the present invention provides a process, wherein the enriched product stream is alternatively processed comprising the steps of:
partially or completely evaporating acetic acid using batch distillation of a low heat history evaporation method such as falling film or agitated thin film dryer, or thin film agitator at atmospheric pressure or by applying vacuum;
reducing acetic acid concentration preferably to 20 to 60% by adding water,
crystallizing using a batch or continuous crystallizer;
separating solid from the mother liquor (technical) by conventional method;
re-dissolving the solid of step (d) in water;
treating with activated carbon or a solid adsorbent such as Dowex L285 and filtering to obtain a clear solution;
recrystallizing the solution of step (f) in a batch or continuous crystallizer;
separating the crystallized solid from mother liquor (pharma) by conventional method;
drying the wet solid of step (h);
milling and blending the dried solid.

In further embodiment of the present invention provides a process, wherein the activated carbon or a solid adsorbent such as Dowex L285 packed in a column in batch or continuous mode is in the range of 2 to 8% of reactant weight of reaction mass.

In still another embodiment of the present invention provides a process, wherein the overall yield of >75%, preferably >80%, most preferably >90% is achieved.

In yet another embodiment of the present invention provides, wherein the technical mother liquor is further processed comprising steps of:
concentrating to 30-99% solid concentration using low heat history equipment such as Falling Film Evaporator (FFE) or Multiple Effect Evaporator (MEE) or ATFD, preferably MEE in a continuous manner;
crystallizing concentrated solid material using a batch or continuous crystallizer;
separating solids from the mother liquor using conventional process;
re-dissolving the solid of step (c) in water;
treating with activated carbon or a solid adsorbent Dowex L285;
recrystallizing in a batch or continuous crystallizer;
separating the solids from mother liquor using conventional methods;
drying the wet solids are using a batch dryer such as a fluid bed dryer or a continuous dryer such as Spin Flash dryer;
milling and blending the dried solid.

In still another embodiment of the present invention provides a process, wherein the technical mother liquor can be recycled to acetylating reaction media with a purge stream to improve over all yield of >80%.

In another embodiment of the present invention provides a process, wherein the pharma mother liquor is further processed comprising the steps of:
concentrating to 30-99% solid concentration using low heat history equipment such as Falling Film Evaporator (FFE) or Multiple Effect Evaporator (MEE) or ATFD, preferably MEE in a continuous manner;
crystallizing concentrated solid material using a batch or continuous crystallizer;
separating solids from the mother liquor using conventional process;
re-dissolving the solid of step (b) in water;
treating with activated carbon or a solid adsorbent Dowex L285;
recrystallizing in a batch or continuous crystallizer;
separating the solids from mother liquor using conventional methods;
drying the wet solids are using a batch dryer such as a fluid bed dryer or a continuous dryer such as Spin Flash dryer;
milling and blending the dried solid.

In still another embodiment of the present invention, wherein the pharma mother liquor is recycled to Tech Crystallizer or pharma charcolization with a purge stream to improve over all yield >82%.

In still another embodiment of the present invention provides, wherein in technical mother liquor containing acetic acid is purified to >99% (glacial) using distillation column.

The present invention provides a process, wherein acetylation may be further effected by modifiers or antioxidants such as zinc powder, sodium metabisulphite, TBHQ, EDTA. Sodium dithionate.

The present invention provides a process, wherein, an organic solvent or mixture of solvent such as benzene, toluene, ethyl acetate and acetic acid etc. may be used.

The present invention provides a process, wherein, the entrainers such as butyl acetate or extracting agents such as ethyl acetate are added to improve separation efficiency of the separation process.

The present invention provides a process, wherein, the technical mother liquor, pharma mother liquor and mother liquors obtained may be purified using distillation column having tray or random packing or structured packing, preferably structured packing, to obtain acetic acid having purity up to 99%.

Reaction

Figure 2:
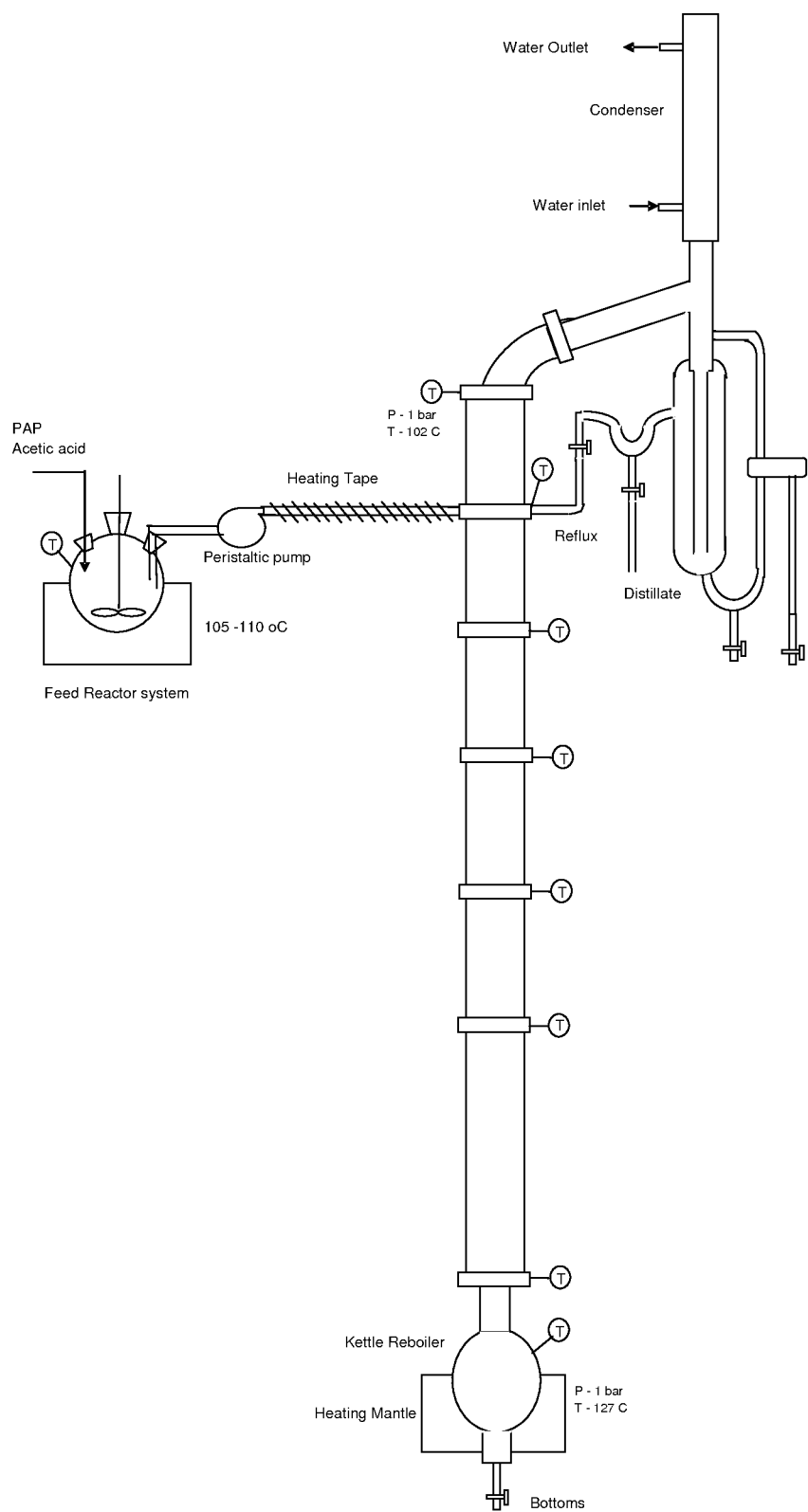

A feed mixture of primary and secondary aromatic amines or salicyclic acid and acetic acid is fed to the reaction zone of reactive separation equipment (FIG. 2) or to the first of series of CSTR or to the first of a series of PFR at a flow rate of 1 ml/min to 120 ml/min and at a feed temperature of 70 to 120° C. The above acetylation reaction can be carried out independently in CSTR or PFR or in reactive separation equipment to completion. At this temperature aromatic amines or salicyclic acid is expected to be fully soluble. The reaction temperature is maintained at a range of 110 to 130° C. and the pressure is at 1 to 3 atmospheres.

Downstream Process

In one case, the reaction mass from reaction equipment is subjected to partial evaporation for acetic acid recovery, water added to dilute the reaction mass and then sent to technical crystallization. In another case it is directly sent to technical crystallization. Technical crystallization is carried out at 10 to 30° C. for 3 to 10 hrs under agitation for proper crystal growth. Crystallized mass is filtered or centrifuged using ANF or Pushar centrifuge or Peeler centrifuge or Basket centrifuge. The tech solid is treated in charcoalizer for color removal followed by a pharma crystallization. Pharma crystallization is also carried out under the same condition of tech crystallization. Crystallized mass is filtered or centrifuged using ANF or Pushar centrifuge or Peeler centrifuge or Basket centrifuge. After solid-liquid separation, pharma solid containing 5 to 8% LOD is dried in fluid bed dryer or spin flash dryer, then milled and blended.

The entire process is depicted in scheme I of FIG. 1.

EXAMPLE 1

In a batch reactor, acetic acid (150 g) was heated to 60-80° C. At that temperature para-aminophenol (100 g) was charged in about 5 to 10 minutes. The mixture was then rapidly heated to 115 to 120° C. over 15 to 20 mins. The reaction was allowed to continue up to 3 hrs. At this stage conversion of 90% was obtained. On further continuation of reaction up to 8 hrs a conversion of >99% was obtained. 120-200 ml of water added for dilution of acid. Reaction mass is then cooled to 10-30° C. for 4 to 7 hrs, crystallized mass was filtered to get the tech paracetamol. The yield of Tech Para is 1.22. Charcoalization of techpara was done by adding 200-500 ml of water and activated carbon of 1-4% of technical mass and heating up to 70-95° C. and maintained for 15-60 min. Activated carbon is filtered and mass is cooled to 5-30° C. over 5-10 hrs. Crystallized mass filtered to get the pharma Paracetamol with LOD of 5-8% dried to <0.5% LOD. The yield of 1.15 to 1.17 is achieved.

Tech ML and Pharma ML are concentrated to 40 to 90 wt % solids by evaporation of acetic acid and water mixture at 50-80° C. and >400 mm Hg vacuum. The concentrated mass cooled to 10-30° C., crystallized mass filtered. This second crop Paracetamol is further treated with charcoal (2-5% of mass) with 2-4 times of water. Second crop yield is in the range of 0.05 to 0.1. An overall yield of this process obtained is in the range of 1.2 to 1.27. The yield is defined here as APAP(wt)/PAP(wt). A percentage yield of 87 to 91.6% is obtained (defined as actual APAP/theoretical APAP*100).

EXAMPLE 2

In another example, the batch reactor is assembled with a distillation packed bed. Acetic acid (150 g) was heated to 60-80° C. At that temperature para-aminophenol (100 g) was charged in about 5 to 10 minutes. The mixture was then rapidly heated to 115 to 120° C. over 15 to 20 mins. The vapor containing water and acetic acid evolved during reaction is sent to the attached distillation column. The water rich overhead stream is collected in a vessel. The bottom stream rich in acetic acid is returned to the reactor. Water removal helped to achieve 90% conversion at reduced time of 2 and half hours. On further continuation of reaction in same manner up to 6 hrs a conversion of >99% was obtained. 120-200 ml of water added for dilution of acid. Reaction mass is then cooled to 10-30° C. for 4 to 7 hrs, crystallized mass was filtered to get the tech paracetamol. The improved yield of Tech Para is 1.26. Charcoalization of techpara was done by adding 200-500 ml of water and activated carbon of 1-4% of technical mass and heating up to 70-95° C. and maintained for 15-60 min. Activated carbon is filtered and mass is cooled to 5-30° C. over 5-10 hrs. Crystallized mass filtered to get the pharma Paracetamol with LOD of 5-8% dried to <0.5% LOD. The yield of 1.17 to 1.19 is achieved. Treating TechML and PharmaML as described in example 1, an overall yield of this process obtained is in the range of 1.22 to 1.29

EXAMPLE 3

Para-aminophenol (100 g) and acetic acid (250 g) were heated to 60-80° C. in pre-reaction vessel and fed to the reactive distillation column at 2 to 30 ml/min flow rate. Column top and bottom temperatures were maintained at 100 and 120° C., respectively. Conversion of 85 to 99% conversion is achieved. 100-180 ml acetic acid recovered from bottom reaction mass and 120-200 ml of water added for dilution. Reaction mass is cooled to 10-30° C., crystallized mass filtered to get the tech Paracetamol. 200-500 ml of water and activated carbon of 1-4% of technical mass are added to technical material and temperature is raised to 70-95° C. and maintained for 15-60 min. Activated carbon is filtered and mass is cooled to 5-30° C. over 5-10 hrs. Crystallized mass filtered to get the pharma Paracetamol with LOD of 5-8% dried to <0.5% LOD. The yield is achieved in the range of 1.15 to 1.24

Tech ML and Pharma ML are concentrated to 40 to 90 wt % solids by evaporation of acetic acid and water mixture at 50-80° C. and >400 mm Hg vacuum. The concentrated mass cooled to 10-30° C., crystallized mass filtered. This second crop Paracetamol is further treated with charcoal (2-5% of mass) with 2-4 times of water. Second crop yield is in the range of 0.05 to 0.11. An overall yield of this process obtained is in the range of 1.2 to 1.35. A percentage yield of 87 to 97.8% is obtained

EXAMPLE 4

A test run was carried out similarly to that described in Example 2 except that N-ethyl p-aminophenol was used instead of PAP. Due to slower kinetics, the flow rate of 1 ml/min 5 ml/min was taken in the reactive distillation column so that the residence time increases for a given column height. Using this tactic >99% conversion was achieved. Similar isolation and purification of the acetylated product were adopted as described in Example 2. An overall yield of this process obtained is in the range of 1.1 to 1.28.

EXAMPLE 5

Salicyclic acid (45 g) and acetic acid (200 g) were heated to 80-90° C. in pre-reaction vessel and fed to the reactive distillation column at 1 to 15 ml/min flow rate. Conversion of 80 to 99% conversion is achieved. The column bottom mass is fed to a distillation vessel where 50 to 100 ml of acetic acid is evaporated under vacuum. To dilute the acid concentration in product mass, 100-200 ml of water is added to help better quality tech Aspirin. The diluted mass is then cooled to 10-30° C., crystallized mass filtered to get the tech Aspirin. 200-500 ml of water and activated carbon of 1-4% of technical mass are added to technical material and temperature is raised to 70-95° C. and maintained for 15-60 min. Activated carbon is filtered and mass is cooled to 5-30° C. over 5-10 hrs. Crystallized mass filtered to get the pharma grade Aspirin with LOD of 5-8% dried to <0.5% LOD. The yield is achieved in the range of 1.05 to 1.15

Tech ML and Pharma ML are concentrated to 40 to 90 wt % solids by evaporation of acetic acid and water mixture at 50-80° C. and >400 mm Hg vacuum. The concentrated mass cooled to 10-30° C., crystallized mass filtered. This second crop Aspirin is further treated with charcoal (2-5% of mass) with 2-4 times of water. Second crop yield is in the range of 0.04 to 0.09. An Overall yield of this process obtained is in the range of 1.09 to 1.24. A percentage yield of 83.5 to 95% is obtained

EXAMPLE 6

Further improvement in isolation and color of the product are made by treating TechML of downstream section in a falling film evaporator in a continuous manner. Shorter residence time (<15 min) and an exposure of product to lower temperature (maximum temperature of 80° C.) during solvent evaporation in the evaporator gives from off-white TechPara to white Techpara. The water required in filtration to wash the Techpara to remove color bodies is therefore cut by 50%. Use of less water for wash improves the yield by 2%.

EXAMPLE 7

A test run was carried out similarly to that described in Example 2 except that a solvent toluene is used as the reaction medium as well as the azeotropic agent to remove water from the reaction system. Better water separation resulted in distillation column height. Using this condition >99% conversion was achieved. Similar isolation and purification of the acetylated product were adopted as described in Example 2. An overall yield of this process obtained is in the range of 1.22 to 1.36. A percentage yield of 88 to 98.1% is obtained

EXAMPLE 8

Further improvement in color of the product is made by treating the TechPara with ethyl acetate. TechPara and ethyl acetate [1:2 ratio (wt/wt)] were stirred in a vessel to the complete dissolution of TechPara at 40 to 70° C. The solution mixture is then cooled to 10 to 15° C. in a crystallizer, Filtered using a separating equipment and product obtained is dried. The product color improves significantly from white to milky white. This process efficiently removed the color bodies.

Variations and modifications which will be obvious and apparent to those skilled in the art may be made in the invention without departing from the spirit and scope thereof.

We claim:

1. A continuous process for the acetylation of primary or secondary aromatic amines to manufacture primary or secondary N-acetylated aromatic amines of formula I:

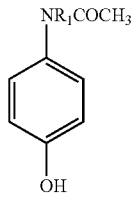

wherein $R_1$ is a hydrogen atom, $C_1$ to $C_4$ alkyl group, or $C_1$ to $C_4$ alkoxy group, the process comprising the steps of:
(a) reacting primary or secondary aromatic amines with acetic acid in Continuous Stirred Tank Reactors (CSTRs) or a Plug Flow Reactor (PFR) to obtain partially converted product stream comprising acetylated amine and starting amine;
(b) subjecting the partially converted product stream as obtained in step (a) to a separation process to obtain an enriched product stream; and
(c) optionally adding very low amount of acetic anhydride to the enriched product stream of step (b).

2. The continuous process as claimed in claim 1, wherein the Continuous Stirred Tank Reactors (CSTRs) or the Plug Flow Reactor (PFR) is used in combination with separation process for the acetylation of primary and secondary N-aromatic amines to manufacture primary and secondary N-acetylated aromatic amines.

3. The continuous process as claimed in claim 2, wherein the separation process is selected from a reactive distillation process, or a membrane separation process, or a pervaporation process, or a chromatographic process.

4. The process as claimed in claim 1, wherein in step (a) the primary aromatic amine or secondary aromatic amine is selected from the group consisting of para amino phenol (PAP) and n-ethyl p-aminophenol.

5. The process as claimed in claim 1, wherein:
i. the concentration of primary or secondary aromatic amines is less than 50% by weight,
ii. the concentration of acetic acid in primary or secondary aromatic amines is greater than 50% by weight,
iii. the separation process is carried out in temperature range from 60 to 140° C. and at about atmospheric pressure.

6. The process as claimed in claim 1, wherein in step (b) the enriched reaction mixture obtained is greater than 60% of product.

7. The process as claimed in claim 1, wherein in step (b) the enriched product stream is processed to obtain the N-acetylated aromatic amines by the following steps:
a. crystallizing by batch or continuous crystallizer;
b. separating the crystallized solids and technical mother liquor (technical) by a conventional method;
c. re-dissolving the crystallized solids thus obtained in water;
d. treating the solution of step (c) with activated carbon or a solid adsorbent and filtering to get a clear solution;
e. recrystallizing the solution of step (d) in batch or continuous crystallizer;
f. separating the crystallized solids from mother liquor (pharma) by conventional method;
g. drying the crystallized solids using a batch dryer or a continuous dryer;
h. milling and blending the dried solid.

8. The process claimed in claim 1, wherein in step (b) the enriched product stream is processed to obtain the N-acetylated aromatic amines by the following steps:
a. partially or completely evaporating acetic acid using batch distillation of a low heat history evaporation method or thin film agitator at atmospheric pressure or by applying vacuum;
b. reducing acetic acid concentration to 20 to 60% by adding water,
c. crystallizing using a batch or continuous crystallizer;
d. separating solid from the mother liquor(technical) by conventional method;
e. re-dissolving the solid of step(d) in water;
f. treating with activated carbon or a solid adsorbent and filtering to obtain a clear solution;
g. recrystallizing the solution of step(f) in a batch or continuous crystallizer;
h. separating the crystallized solid from mother liquor (pharma) by conventional method;
i. drying the wet solid of step(h);
j. milling and blending the dried solid.

9. The process as claimed in claim 7 or 8, wherein the activated carbon or a solid adsorbent packed in a column in batch or continuous mode is in the range of 2 to 8% of reactant weight of reaction mass.

10. The process as claimed in claim 1, wherein the overall yield of >75% is achieved.

11. The process as claimed in claim 7 or 8, further comprising recovering final traces of the N-acetylated aromatic amines from the technical mother liquor of step (b) of claim 7 or step (d) of claim 8, comprising steps of:

a. concentrating to 30-99% solid concentration using low heat history equipment in a continuous manner;
   b. concentrating solids crystallized using a batch or continuous crystallizer;
   c. separating solids from the mother liquor using conventional process;
   d. re-dissolving the solid of step (c) in water;
   e. treating with activated carbon or a solid adsorbent;
   f. recrystallizing in a batch or continuous crystallizer;
   g. separating the solids from mother liquor using conventional methods;
   h. drying the wet solids are using a batch dryer or a continuous dryer;
   i. milling and blending the dried solid.

12. The process as claimed in claim 7 or 8, further comprising the step of recycling the technical mother liquor of step (b) of claim 7 or step (d) of claim 8 to acetylating reaction media with a purge stream to improve over all yield of >80%.

13. The process as claimed in claim 7 or 8, further comprising recovering final traces of the N-acetylated aromatic amines from the pharma mother liquor of step (f) of claim 7 or step (h) of claim 8, comprising the steps of:
   a. concentrating to 30-99% solid concentration using low heat history equipment in a continuous manner;
   b. concentrating solids crystallized using a batch or continuous crystallizer;
   c. separating solids from the mother liquor using conventional process;
   d. re-dissolving the solid of step(b) in water;
   e. treating with activated carbon or a solid adsorbent;
   f. recrystallizing in a batch or continuous crystallizer;
   g. separating the solids from mother liquor using conventional methods;
   h. drying the wet solids are using a batch dryer or a continuous dryer;
   i. milling and blending the dried solid.

14. The process as claimed in claim 7 or 8, further comprising the step of recycling the pharma mother liquor of step (f) of claim 7 or step (h) of claim 8 to Tech Crystallizer or pharma charcolization with a purge stream to improve over all yield of >82%.

15. The process as claimed in claim 7 or 8, further comprising the step of purifying the technical mother liquor containing acetic acid of step (b) of claim 7 or step (f) of claim 8 to obtain >99% (glacial) using a distillation column.

16. The process as claimed in claim 1, wherein acetylation may be further effected by modifiers or antioxidants.

17. The process as claimed in claim 1, wherein an organic solvent or mixture of solvent is used.

18. The process as claimed in claim 1, wherein entrainers or extracting agents are added to improve separation efficiency of the separation process in step (b).

19. The process as claimed in claim 7 or 8, wherein the technical mother liquor, pharma mother liquor and mother liquors obtained are purified using distillation column having tray or random packing or structured packing to obtain acetic acid having purity up to 99%.

20. The process as claimed in claim 11, wherein the technical mother liquor, pharma mother liquor and mother liquors obtained may be purified using distillation column having tray or random packing or structured packing to obtain acetic acid having purity up to 99%.

21. The process as claimed in claim 13, wherein the technical mother liquor, pharma mother liquor and mother liquors obtained may be purified using distillation column having tray or random packing or structured packing to obtain acetic acid having purity up to 99%.

* * * * *